| United States Patent [19] | [11] Patent Number: 4,873,077 |
|---|---|
| Thompson et al. | [45] Date of Patent: Oct. 10, 1989 |

[54] LIQUID FIBER WRAP FINGERNAIL REINFORCEMENT COMPOSITION

[76] Inventors: Steven L. Thompson, 301 N. Pine Island Rd., Plantation, Fla. 33324; Melvin K. Silverman, 1460 SE. 15th St., Fort Lauderdale, Fla. 33316

[21] Appl. No.: 99,200

[22] Filed: Sep. 21, 1987

[51] Int. Cl.$^4$ .............................................. A61K 7/04
[52] U.S. Cl. ........................................ 424/61; 424/401
[58] Field of Search ........................................... 424/61

[56] References Cited

U.S. PATENT DOCUMENTS 4,402,935  9/1983  Gordon et al. ........................ 424/61
4,712,571  12/1987  Remz .................................... 424/61

FOREIGN PATENT DOCUMENTS 1956775  11/1969  Fed. Rep. of Germany ........ 424/61
41-11000  6/1966  Japan .................................... 424/61
1177420  6/1967  United Kingdom ................. 424/61
1193153  5/1970  United Kingdom ................. 424/61

*Primary Examiner*—Thurman K. Page
*Assistant Examiner*—P. L. Prater
*Attorney, Agent, or Firm*—Alice Chen

[57] ABSTRACT

An improved nail hardener comprises a nitrocellulose-base nail lacquer and fiber glass, 10 microns in diameter by 800 microns long. The nail hardener forms a film approximately five times as strong as the film formed by conventional nail hardener. A method of strengthening and protecting fingernails against chipping and cracking and concealing imperfections of the nails by coating said nail with a nail hardener containing fiber glass is also provided.

5 Claims, No Drawings

LIQUID FIBER WRAP FINGERNAIL REINFORCEMENT COMPOSITION

BACKGROUND OF THE INVENTION

Field of Invention

This invention relates to a new human nail hardener and more specifically a nail hardener containing fiber glass, usable as a base coat to the nails for strengthening and protecting nails from chipping and splitting as well as for concealing imperfections of the nails.

The application of a hardening undercoat to human nails before the application of a final coat of nail polish is known in the prior art. Such undercoats are generally used for nail surfacing and repair purposes.

U.S. Pat. No. 4,267,852 discloses a method and composition for enhancing the growth and strength of fingernails and toenails including the application of a protein-containing composition directly to the nails, followed by the application of a coating of silicon cream and lacquer containing nylon fibers.

U.S. Pat. No. 4,157,095 discloses the use of a fiber-glass sheet as a base for an artificial nail. The artificial nail is glued to the nail with acrylic resin, and a final coat of acrylic resin is applied to the artificial nail.

Other fabrics, such as flax, linen and silk are applied to human nails with adhesives and hardeners, to create artificial nails, as disclosed in U.S. Pat. No. 4,627,453.

Nail hardeners on the market are generally used to seal and protect nail polish previously applied to the nail. They do not protect or strengthen the nails themselves against splitting or chipping.

Other liquid compositions containing nylon fibers are used to repair nails bu do not provide much mechanical strength for the protection of nails.

Artificial fingernails, though they protect the natural nails, are awkward and time consuming to apply. Therefore, there is a need for an improved nail hardener which is easy to apply.

It is an object of this invention to provide a strong protective nail hardener.

Another object of this invention is to provide a nail hardener which covers splits and unevenness in fingernails to present a smooth appearance.

It is a further object of this invention to provide a method of protecting fingernails or toenails against splitting, and which conceals imperfections.

SUMMARY OF THE INVENTION

These and other objects and advantages in accordance with the present invention will be apparent from the following description.

A nail hardener in accordance with the present invention will be apparent from the following description.

A nail hardener in accordance with the present invention comprises a suspension of about one part of finely divided fiber glass in about 5 parts of nail lacquer, by volume, said nail lacquer being a solution of nitrocellulose, a resin and a plasticizer of one or more solvents, which evaporates upon application of this nail hardener to the nails, leaving a hardener and strong coating on the nails.

A method of strengthening and protecting fingernails against splitting and chipping, and the covering of imperfections of the nails include coating said nails with a new nail hardener comprising a suspension of one part of finely divided fiber glass by volume and about 5 parts of a nail lacquer by volume.

DESCRIPTION OF PREFERRED EMBODIMENT

The basic ingredients of the nail lacquer used in this invention are commercially available. They include nitrocellulose, which is principally a film former; a natural or synthetic resin which promotes better depth, gloss and adhesion of the resulting film to the nails; and a plasticizer which gives control, flexibility and elongation of the film and solvents including dilutents.

Nail lacquer formulas are generally nitrocellulose based, but other lacquer bases such as cellulose acetate, ethyl cellulose, and cellulose acetate-butyrate may also be used.

The fiber glass used in this invention is preferably filaments having a diameter of about 10 microns and an 800 micron length being preferred.

This finely divided fiber glass is dispersed in the nail lacquer at room temperature, with stirring, to form a uniform suspension. The nail lacquer should have a viscosity between 300–500 cps. (centiposises) at room temperature.

The proportion of fiber glass to nail lacquer ranges from 1:8 to 1:3 by volume, which is about 16% to 33%. The preferred ratio of fiber glass to nail lacquer is 10% to 20% by weight.

Generally, the nail hardener in accordance with his invention does not contain any pigments, since a final coat of nail polish containing pigment will be applied over it; however, pigment may optionally be added to the nail hardener of this invention.

In another embodiment of this invention, the nail hardener further comprises a silicone liquid which is sold under the name of Union Carbide Silicone Fluid Y-7676. The silicone fluid is to enhance the smoothness of the dried film after evaporation of the solvent of the hardener and to enhance its moisture resistance.

The nail hardener of this invention is applied directly to the fingernails before the final coats of nail polish is applied. This fiber glass contained in the nail hardener forms a lattice structure which significantly increases the mechanical strength of the film of the hardener and also serves to protect the fingernails against splitting and chipping.

Moreover, the nail hardener of this invention is capable of concealing imperfections in fingernails such as such as splits, cracks, and ridges by forming a smooth surface for the application of nail polish.

A hardness test involving scratching confirms the hardened film of the present invention is about five times as hard as that of a conventional hardener.

The following are examples of nail hardener compositions in accordance with the present invention:

EXAMPLE 1

| | |
|---|---|
| Nitrocellulose | 130 grams |
| Ethyl cellulose | 16 grams |
| Tricresyl phosphate | 24 grams |
| Dihydrometyl abietate (resin) | 34 grams |
| Dibutyl phtalate | 50 grams |
| Denatured alcohol | 83.5 grams |
| Xylol | 21 grams |
| Ethyl acetate | 260 grams |
| Butyl acetate | 113 grams |
| Amyl acetate | 112 grams |
| Fiber glass | 94 grams |

EXAMPLES 2

| | |
|---|---|
| Nitrocellulose | 10-16% by wt |
| Tolune sulfonamide formaldehyde (Santolite) | 3-10% |
| Dibutyl phthalate | 3.75-4.0% |
| Butyl acetate | 11-30% |
| Ethyl or isoproyl alcohol | 6.4-10% |
| Toluene and | 37-43% |
| Fiber glass | 10-20% |

It is to be understood that in the above formulae, nitrocellulose is given on a solvent-free basis. A nitrocellulose referred to as "RS ½ sec" is preferred because of its high nitrogen content and its high compatibility with many resins and solvents.

The viscosity of the formulae ranges from 300 to 450 cpc.

Either natural or synthetic resins other than those listed above may also be used, e.g. polyvinyl acetate, butyrates, dammar, shellac or acryl sulfonamide-formaldehyde, the last resin being preferred because it enhances depth, gross, and water resistance of the resulting film of the hardener.

Plasticizers, other than those listed above which may be used in this invention are butyl phtalate, butyl glycolate, dioctyl phtalate, triphenyl phosphate, camphor and castor oil.

Solvents other than those listed above, which may be used in the formulae of this invention, include xylene, n-butyl alcohol, acetone and methyl cellosolve.

It is to be understood that any suitable combination of nail lacquer components known to the prior art may be used as a medium for the nail hardener of this invention. The addition of finely divided fiber glass, approximately 10 microns in diameter by 800 microns long, by suspension thereof in either of the above formulae confers upon the fingernail coating significantly increased hardness and mechanical strength. Thus the nail hardener of this invention is unique in that in addition to its strength, it also covers imperfections of nail and provides a smooth surface to be coated with nail polish. Consequently, the adhesion of the nail polish to the underlying nail hardener film is increased so that the nail polish lasts longer.

For accelerated drying of the nail hardener one drop of a cyanoacrylate glue, such as alpha cyanoacrylate, may be placed upon undried nail hardener, and mixing thereinto.

Although the preferred compositions and method have been described above, it should be understood that various substitutions, alterations and modifications may become apparent to those skilled in the art. Thus these modifications may be made without departing from the spirit and scope of the invention as defined in the appended claims.

What is claimed is:

1. A fingernail reinforcement composition, comprising:
    a nitrocellulose-based nail lacquer having plasticizer, resin and solvent, and glass fibers suspended in said nail lacquer, in which the proportion of glass fiber to said nitrocellulose based formula is in the range of 1:3 to 1:8, and said glass fiber possesses dimensions of about 10 microns in diameter and about 800 microns in length.

2. The nail hardener of claim 1 wherein the plasticizer is selected from a group consisting of dibutyl phtalate, tricresylphosphate, butyl phythalylbutyl glycolate, dicetyl phthalate, triphenyl phosphate, camphor and castor oil.

3. The nail hardener of claim 1 wherein the resin is selected from the group consisting of polyvinyl acetate butyrate, and acryl sulfonamide-formaldehyde.

4. The nail hardener of claim 1 wherein the solvents are selected from the group consisting of alkyl alcohol of 1-4 carbons, and low alkyl acetates of 1-4 carbons.

5. The nail hardener of claim 3 wherein the solvent further comprises toluene.

* * * * *